United States Patent [19]

Kim

[11] Patent Number: 5,551,949

[45] Date of Patent: *Sep. 3, 1996

[54] INFRARED MASSAGE DEVICE

[75] Inventor: Yong Kim, Seoul, Rep. of Korea

[73] Assignee: Interport International, Inc., Corona Del Mar, Calif.

[*] Notice: The term of this patent shall not extend beyond the expiration date of Pat. No. 5,176,130.

[21] Appl. No.: 356,651

[22] Filed: Dec. 2, 1994

Related U.S. Application Data

[63] Continuation of Ser. No. 961,104, Oct. 13, 1992, abandoned, which is a continuation of Ser. No. 775,295, Oct. 10, 1991, Pat. No. 5,176,130.

[51] Int. Cl.[6] .................................................. A61H 1/00
[52] U.S. Cl. ............................. 601/15; 601/70; 601/72
[58] Field of Search .................................... 601/15, 70–74, 601/69, 78–81, 17, 18, 139–142; 250/495.1, 504 H, 504 R

[56] References Cited

U.S. PATENT DOCUMENTS

| | | | |
|---|---|---|---|
| 2,661,736 | 12/1953 | Schwartz | 601/80 X |
| 2,675,800 | 4/1954 | Voorhees et al. | 126/36 |
| 2,809,631 | 10/1957 | Smith et al. | 601/81 |
| 2,974,664 | 3/1961 | McNair | 601/72 X |
| 3,648,706 | 3/1972 | Holzen | 128/395 |
| 3,699,952 | 10/1972 | Waters et al. | 601/18 |
| 3,710,785 | 1/1973 | Hilger | 128/36 |
| 4,298,806 | 11/1981 | Herold | 250/504 H |
| 4,300,556 | 11/1981 | Ochi et al. | 128/256 |
| 4,497,313 | 2/1985 | Kurosawa | 128/24.1 |
| 4,560,883 | 12/1985 | Kerschgens | 250/504 R |
| 4,646,725 | 3/1987 | Moasser | 128/24 A |
| 4,655,232 | 4/1987 | Ficke | 132/79 |
| 4,757,806 | 7/1988 | Muchisky et al. | 128/36 |
| 4,797,840 | 1/1989 | Fraden | 364/557 |
| 4,854,730 | 8/1989 | Fraden | 374/164 |
| 4,936,302 | 6/1990 | Abernathy | 606/158 |
| 4,948,974 | 8/1990 | Nelson et al. | 250/358.1 |
| 4,983,851 | 1/1991 | Masuda et al. | 250/493.1 |
| 5,010,452 | 4/1991 | Krebser et al. | 362/19 |
| 5,095,901 | 3/1992 | Davitashvili et al. | 128/395 |
| 5,104,392 | 4/1992 | Kittrell et al. | 606/15 |
| 5,165,131 | 11/1992 | Staar | 601/142 X |
| 5,176,130 | 1/1993 | Kim | 128/36 |

Primary Examiner—Robert A. Hafer
Assistant Examiner—Brian E. Hanlon
Attorney, Agent, or Firm—Stetina Brunda & Buyan

[57] ABSTRACT

A heated massage therapy device has a hand-held housing, a mechanical vibration generator disposed within the housing, the mechanical vibration being transmitted to at least a heat-conductive, preferably infrared transparent portion thereof, and at least one source of infrared radiation disposed within the housing, the infrared radiation being applied to at least the heat-conductive portion of the housing. A corresponding number of first fresnel lenses formed in the heat portion of the housing concentrates infrared radiation such that it may more efficiently be applied to the user. Second fresnel lenses may be formed about all of the individual infrared radiation sources as a group to further concentrate the infrared radiation applied to the user. An infrared reflective member disposed proximate the infrared radiation sources reflects infrared radiation not incident upon the heat-conductive portion of the housing theretoward. Each of the infrared radiation sources may be substantially surrounded by a thermal conduction member which absorbs the infrared radiation radiated therefrom and conducts the heat generated thereby to the heat-conductive portion of the housing. Thus, the heated massage therapy device of the present invention provides a thermally efficient and effective means of applying infrared radiation in combination with mechanical vibration to selected portions of a user's anatomy.

10 Claims, 2 Drawing Sheets

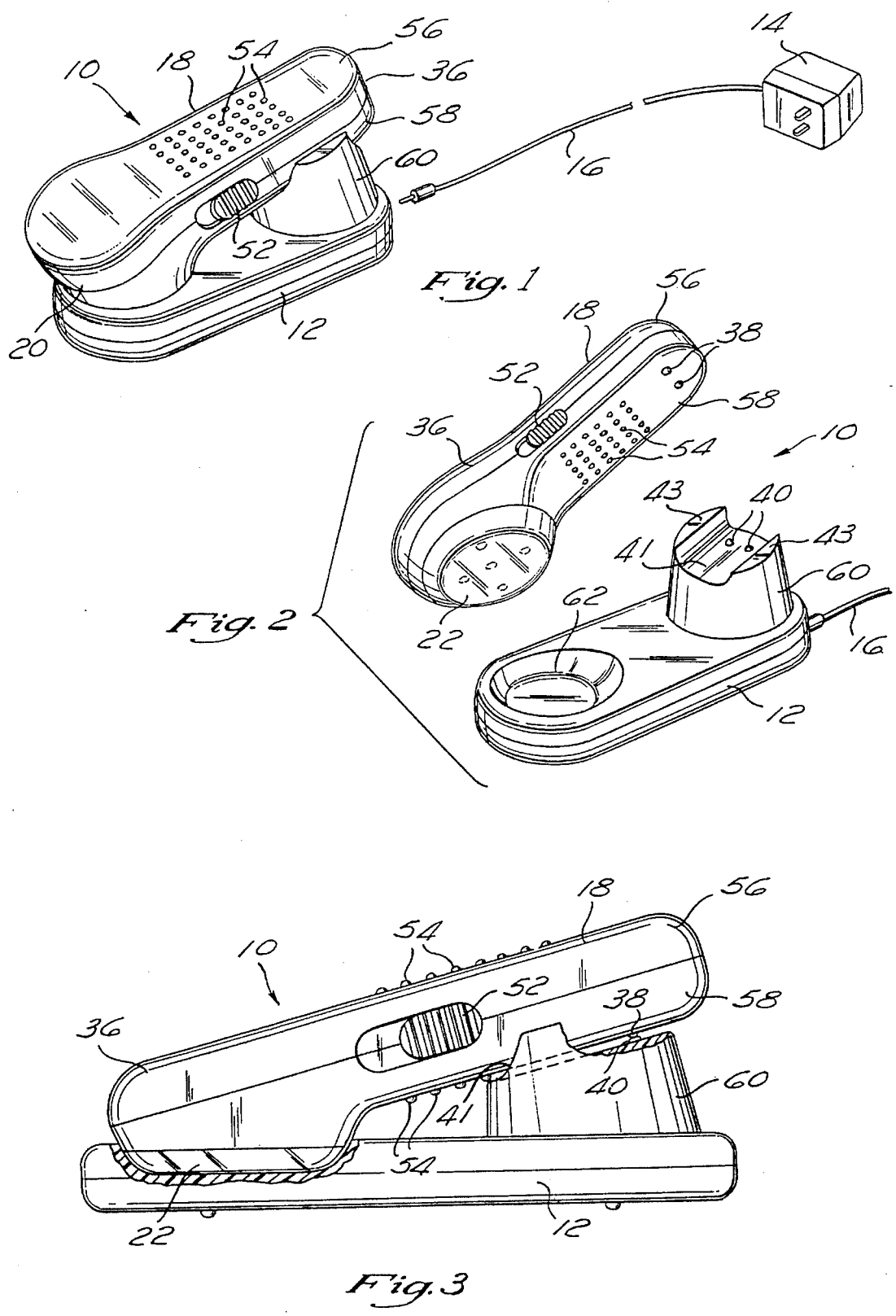

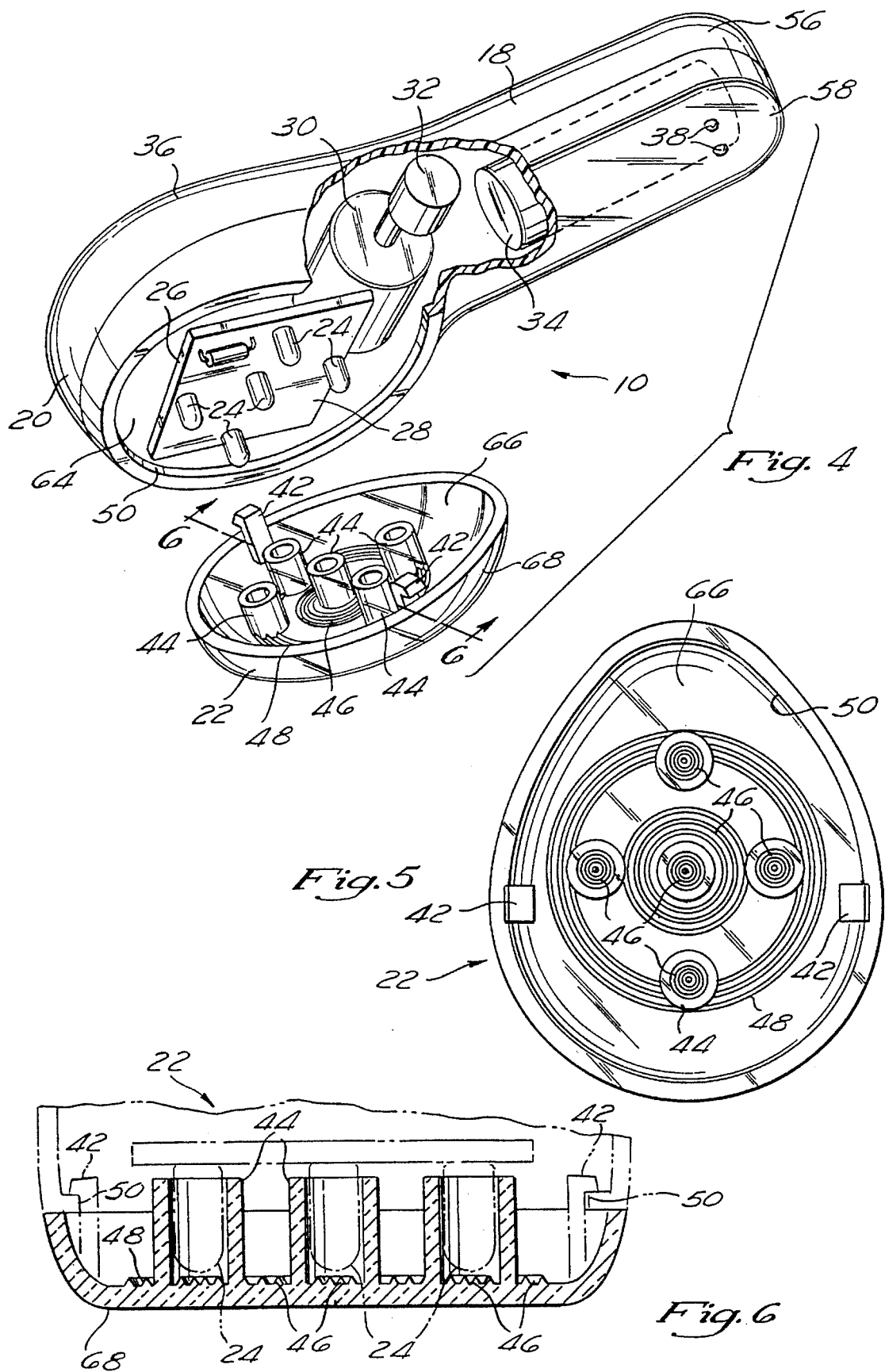

INFRARED MASSAGE DEVICE

This application is a continuation of application Ser. No. 07/961,104, filed Oct. 13, 1992, now abandoned, which is a continuation appln. of Ser. No. 07/775,295, filed Oct. 10, 1991, now U.S. Pat. No. 5,176,130, issued Jan. 5, 1993.

FIELD OF THE INVENTION

The present invention relates generally to therapeutic devices, and more particularly to a heated massage therapy device for applying both heat and mechanical vibration to selected anatomical portions of a user's body.

BACKGROUND OF THE INVENTION

Massage devices for applying mechanical vibration to selected anatomical portions of a user's body are well known. Such massage devices typically comprise an electric motor having an eccentric weight attached to the armature thereof for generating mechanical vibration which is then transmitted to the housing of the device from which it may be applied to the user. Contemporary massage therapy devices are recognized to provide increased blood flow, nerve stimulation, and muscle relaxation. They are believed to improve the complexion and to reduce skin wrinkling. Those skilled in the art will recognize that many such therapeutic uses for vibratory massage therapy devices exist.

The benefits of heat therapy in various medical and cosmetic applications are likewise well known. Heat therapy is commonly performed to increase circulation and promote healing of various traumatic injuries, such as sprains, strains, and wounds. Heat may also be used in cosmetic applications to improve the complexion and reduce wrinkling.

Although massage therapy devices are known which apply both heat and mechanical vibration to selected portions of a user's anatomy, the heat is typically applied through a body-contacting heat-conductive member which does not provide for specific localization or concentration of the heat upon the heat-conductive member in a manner which optimizes the potential therapeutic benefits achievable therefrom. That is, generally a heating element or infrared lamp causes an overall warming of the heat-conducting member in a manner which generally results in substantially uniform heating thereof. However, it is believed that by concentrating the heat to specific regions of the heat conductive member of the massage therapy device, optimum therapeutic results are provided in a manner which most efficiently utilizes the heat generated thereby.

For example, undesirable heat loss to the remainder of the housing is minimized by concentrating the heat toward the center of the heat-conducting member, away from the edges thereof which contact the remainder of the housing. Such efficiency is particularly important in rechargeable devices wherein efficient use of the power supplied by the device's rechargeable batteries is of paramount importance. As such, although the prior art has recognized the benefits of administering vibration and heat therapy, the proposed solutions have to date been ineffective in providing a satisfactory remedy.

SUMMARY OF THE INVENTION

The present invention specifically addresses and alleviates the above-mentioned deficiencies associated in the prior art. More particularly, the present invention comprises a heated massage therapy device having a hand-held held housing, a means for generating mechanical vibration disposed within the housing, the mechanical vibration being transmitted to at least a heat-conductive, preferably infrared transparent, portion or window thereof, and at least one source of infrared radiation disposed within the housing, the infrared radiation being applied to at least the window of the housing.

First fresnel lenses formed in the window of the housing concentrate infrared radiation such that it may more efficiently be applied to the user. Second fresnel lenses may be formed about all of the individual infrared radiation sources as a group to further concentrate the infrared radiation applied to the user. Thus, heat is concentrated within a portion of the window, i.e. the center, where it is most efficiently transferred to a user and heat loss to the remainder of the housing is thereby minimized.

An infrared reflective member disposed proximate the infrared radiation sources reflects infrared radiation not incident upon the heat-conductive window of the housing theretoward. This increases the efficiency of heat transfer from the infrared sources to the window. Each of the infrared radiation sources may be substantially surrounded by a thermal conduction member or hollow post which absorbs the infrared radiation radiated therefrom and conducts the heat generated thereby to the heat-conductive window of said housing. This further increases the efficiency of heat transfer from the infrared sources to the window. Thus, the heated massage therapy device of the present invention provides a thermally efficient and effective means of applying infrared radiation in combination with mechanical vibration to selected portions of a user's anatomy.

These, as well as other, advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 1 is a perspective view of the heated massage therapy device of the present invention showing the device cradled within its stand and also depicting a standard power supply connectable thereto;

FIG. 2 is the heated massage therapy device and stand of FIG. 1 depicting the device removed from the stand;

FIG. 3 is an elevational side view of the heated massage therapy device;

FIG. 4 is an enlarged perspective view of the heated massage therapy device having the lens removed therefrom and showing the lamps, the motor, and the battery;

FIG. 5 is an enlarged bottom view (inside looking out) of the lens of FIG. 4; and FIG. 6 is a cross-sectional side view of the lens of FIG. 4 taken along lines 6 thereof.

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

The heated massage therapy device of the present invention is illustrated in FIGS. 1–6 which depict a presently preferred embodiment of the invention. Referring now to FIGS. 1–3, the heated massage therapy device 10 is comprised generally of a housing 36 having a handle portion 18 and a head portion 20 and preferably divided into upper 56 and lower 58 separately molded housing sections. A plurality of nipples 54 are formed upon the handle portion 18 of both the upper 56 and lower 58 housing sections.

The heated massage therapy device 10 is cradled upon a base 12. A power supply 14 supplies electrical power through a power cord 16 to the base 12. A switch 52, preferably a three-position on-off switch, permits the user to select either vibration or vibration with infrared heat. Those skilled in the art will recognize that various switch means may be provided wherein the user may select various combinations of vibration and infrared heat, including variations in intensity of either. The stand 12 is comprised of an elevated portion 60 and a recess 62 which receive the heated massage therapy device 10 such that it may be conveniently grasped about the handle portion 18 thereof. A groove 41 formed within the elevated portion 60 receives a portion of the handle portion 18 of the heated massage therapy device 10. The groove 41 defines ears 43 disposed upon either side thereof which cradle the handle portion 18 of the heated massage therapy device 10 to prevent its inadvertent removal therefrom.

Electrical contacts 38 formed upon the handle portion 18 of the heated massage therapy device mate with corresponding electrical contacts 40 formed upon the elevated portion 60 of the stand 12. The power cord 16 preferably supplies electrical power through conductors (not shown) disposed within the base 12 directly to the contacts 40 such that no electrical components are located within the stand 12.

Referring now to FIGS. 4–6, an electric motor 30 powered by a rechargeable battery 34 effects rotation of an eccentric mass 32. Infrared radiation sources or lamps 24 are disposed upon a circuit board 26 having an infrared reflective surface 28. A lip 50 is formed about the head portion 20, thus defining the periphery of an opening 64 to which infrared transparent body portion or removable window 22 attaches via detents 42. A heat-conductive portion of the housing 36 or window 22 is preferably comprised of an infrared transparent material. The window 22 is further comprised of thermal conduction members or hollow posts 44 extending downward therefrom which receive the lamps 24 therein such that the lamps radiate a substantial portion of their infrared radiation thereupon.

Individual fresnel lenses 46 are formed upon the inner surface 66 of the window 22. A group fresnel lens 48 surrounds the individual fresnel lenses 46 and is likewise formed upon the inner surface 66 of the window 22. Thus, the outer surface 68 of the window 22 may be formed in a relatively smooth fashion.

Having thus described the structure of the heated massage therapy device 10 of the present invention, it may be useful to describe the operation thereof. The heated massage therapy unit 10 is normally stored upon the stand 12 with the power supply 14 plugged into an electrical outlet. Thus, the rechargeable battery 34 receives electricity through contacts 38 and 40 to facilitate recharging thereof.

A user may simply grasp the handle portion 18 of the heated massage therapy device 10, contacting the nipples 54 thereof. The nipples 54 formed upon the handle 18 facilitate firm grasping of the handle portion 18, even when the user's hand is slippery, as when contemporaneously applying lotion or medication therewith. The switch 52 is moved to the desired setting whereby vibration and/or infrared heat may be applied to selected portions of the user's anatomy. Placing the switch 52 in a position to effect actuation of the electric motor 30 causes rotation of the armature thereof, such that the eccentric weight 32 causes the generation of vibratory motion, particularly within the head portion 20 of the heated massage therapy device. This vibratory motion is transferred to the desired anatomical portion of the user's body through the smooth outer surface 68 of the window 22.

Positioning the switch 52 such that the lamps 24 are illuminated causes infrared radiation to be radiated therefrom. A substantial portion of the infrared radiation radiated therefrom is absorbed by the thermal conduction members or hollow posts 44 and therefrom conducted to the outer surface 68 of the heat-conductive window 22 for application to selected anatomical portions of the user's body. A portion of the infrared radiation not immediately absorbed by the hollow posts 44 is incident upon the infrared reflective surface 28 of the circuit board 26 and reflected therefrom back toward the inner surface 66 and hollow posts 44 of the window 22. A substantial portion of this reflected radiation is then absorbed by the hollow posts 44 and inner surface 66 of the window 22 from which it may be thermally conducted to the outer surface 68 thereof.

Individual fresnel lenses 46 formed about each hollow post 44 tend to concentrate that infrared radiation incident upon the fresnel lens 46 to form localized regions of increased temperature upon the central portion of the outer surface 68 of the heat-conductive window 22. The group fresnel lens 48 surrounding each of the individual fresnel lenses 46 tends to concentrate a portion of the infrared radiation not incident upon the individual fresnel lenses 46 to cause a further increase in the temperature of the central portion of the outer surface 68 of the window 22. Thus, the efficiency of the infrared radiation absorption and concentration process is substantially improved thereby.

It is understood that the exemplary heated massage therapy device described herein and shown in the drawings represents only a presently preferred embodiment of the invention. Indeed, various modifications and additions may be made to such embodiment without departing from the spirit and scope of the invention. For example, the precise arrangement of the lamps need not be precisely as illustrated and described, rather any configuration which facilitates concentration of the infrared radiation emitted thereby upon the outer surface 68 of the window 22 is likewise suitable. Also, the nipples 54 need not be configured precisely as illustrated, but rather may be configured in any pattern which facilitates the ready grasping and control of the heated massage therapy device. Thus, these and other modifications may be obvious to those skilled in the art and may be implemented to adapt the present invention for use in a variety of different applications.

What is claimed is:

1. A heated message therapy device comprising:

a) a hand-held housing having an infrared transparent portion;

b) means for generating mechanical vibration disposed within said housing, the mechanical vibration being transmitted to at least the infrared transparent portion of said housing, said infrared transparent portion being substantially transparent to infrared radiation;

c) at least one source of infrared radiation disposed within said housing, the infrared radiation being applied to at least the infrared transparent portion of said housing;

d) a number of first fresnel lenses, the number of first fresnel lenses corresponding to the number of sources of infrared radiation, formed in the infrared transparent portion of said housing for concentrating said infrared radiation;

e) an infrared radiation reflecting member disposed proximate said infrared radiation sources for reflecting at least one infrared radiation from said infrared radiation source toward the infrared transparent portion of said housing; and f) at least one thermal conduction member, the number of thermal conduction members corresponding substantially to the number of infrared radiation sources, substantially surrounding individual ones of said infrared radiation sources to absorb infrared radiation radiated therefrom and transfer the heat generated thereby to the infrared transparent portion of said housing.

2. The heated massage therapy device as claimed in claim 1 wherein the hand-held housing defines a handle, and wherein the device further comprises a cradle configured to receive said hand-held housing, said cradle configured to facilitate easy grasping of said handle.

3. The heated massage therapy device as recited in claim 2 wherein said source of radiated infrared radiation comprises at least one lamp, and said reflecting member comprising a reflected surface formed upon a circuit board upon which said at least one source of infrared radiation is disposed.

4. The heated massage therapy device as recited in claim 2 further comprising a plurality of nipples formed upon said handle to facilitate holding thereof, said cradle being configured so as to facilitate grasping said handle via said nipples.

5. The heated massage therapy device as recited in claim 2 further comprising:

a) at least one battery disposed within said housing;

b) electrical contacts formed upon said housing; and c) electrical contacts formed upon said cradle configured to provide electrical interconnection to the electrical contacts formed upon said housing so as to facilitate charging of said at least one battery.

6. A heated message therapy device comprising:

a) a hand-held housing having a substantially infrared transparent portion thereof, said infrared transparent portion being substantially transparent to infrared radiation;

b) means for generating mechanical vibration being transmitted to at least the substantially infrared transparent portion of said housing;

c) at least one source of infrared radiation disposed within said housing, the infrared radiation being applied to at least the substantially infrared transparent portion of said housing; and d) a number of first fresnel lenses, the number of first fresnel lenses corresponding to the number of sources of infrared radiation, formed in the substantially infrared transparent portion of said housing for concentrating said infrared radiation.

7. The heated massage therapy device as claimed in claim 6 wherein the hand-held housing defines a handle, and wherein the device further comprises a cradle configured to receive said hand-held housing, said cradle configured to facilitate easy grasping of said handle.

8. The heated massage therapy device as recited in claim 7 wherein said source of radiated infrared radiation comprises at least one lamp and further comprising a reflecting member configured to reflect infrared radiation radiated by said at least one source of infrared radiation toward the infrared transparent portion of said housing, said reflecting member comprising a reflected surface formed upon a circuit board upon which said at least one source of infrared radiation is disposed.

9. The heated massage therapy device as recited in claim 7 further comprising a plurality of nipples formed upon said handle to facilitate holding thereof, said cradle being configured so as to facilitate grasping said handle via said nipples.

10. The heated massage therapy device as recited in claim 7 further comprising:

a) at least one battery disposed within said housing;

b) electrical contacts formed upon said housing; and c) electrical contacts formed upon said cradle configured to provide electrical interconnection to the electrical contacts formed upon said housing so as to facilitate charging of said at least one battery.

* * * * *